(12) United States Patent
Abe

(10) Patent No.: US 8,744,156 B2
(45) Date of Patent: Jun. 3, 2014

(54) PHOTOGRAPHIC INFORMATION PROCESSING APPARATUS AND PHOTOGRAPHIC INFORMATION PROCESSING METHOD

(75) Inventor: Masahiro Abe, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 658 days.

(21) Appl. No.: 12/764,013

(22) Filed: Apr. 20, 2010

(65) Prior Publication Data

US 2010/0272343 A1 Oct. 28, 2010

(30) Foreign Application Priority Data

Apr. 24, 2009 (JP) ................................. 2009-106388

(51) Int. Cl.
*G06K 9/00* (2006.01)
*G06T 7/00* (2006.01)

(52) U.S. Cl.
CPC .................................. *G06T 7/0012* (2013.01)
USPC ........................................................ 382/131

(58) Field of Classification Search
CPC ....... G06T 1/00; G06T 7/0012; G06T 11/003; G06T 11/005; A61B 5/003; A61B 19/50
USPC .......... 382/131, 100, 149; 229/67.1; 705/2, 3; 600/300
See application file for complete search history.

(56) References Cited

U.S. PATENT DOCUMENTS

| | | |
|---|---|---|
| 5,671,359 A | 9/1997 | Godlewski et al. |
| 2003/0156765 A1 | 8/2003 | Yamamichi |
| 2007/0016454 A1 * | 1/2007 | Tipirneni ........................ 705/3 |
| 2007/0078674 A1 | 4/2007 | Weinberg et al. |
| 2007/0130190 A1 * | 6/2007 | Yoshikawa .................... 707/102 |
| 2007/0226005 A1 * | 9/2007 | Smith et al. ...................... 705/2 |

FOREIGN PATENT DOCUMENTS

| | | |
|---|---|---|
| EP | 952726 A1 | 10/1999 |
| JP | 2002-215809 A | 8/2002 |
| JP | 2002245435 A | 8/2002 |
| JP | 2003114933 A | 4/2003 |
| JP | 2003290200 A | 10/2003 |
| JP | 2004272402 A | 9/2004 |
| JP | 2008188096 A | 8/2008 |

\* cited by examiner

*Primary Examiner* — Michelle L Le
(74) *Attorney, Agent, or Firm* — Canon USA Inc. IP Division

(57) ABSTRACT

A photographic information processing apparatus corrects photographic information based on temporarily determined photographic information relating to a photographing operation. The photographic information processing apparatus includes a photographic information correction determination unit determines whether correction of the photographic information is required based on an operation by an operator, an image data acquisition unit detects an X-ray having penetrated a body of a patient and acquires image data based on the detected X-ray, a photographic information correction unit corrects the temporarily determined photographic information based on patient information of the patient in a case where the correction of the photographic information is determined to be required, and an image data output unit outputs the image data after the correction of the temporarily determined photographic information is completed. The acquired image data is prevented from being output unless the temporarily determined photographic information is corrected.

26 Claims, 11 Drawing Sheets

FIG.6

| PID | Name | DOB | Sex | Acc# |
|---|---|---|---|---|
| 13579 | Taro Casnon | 1955.12.12 | M | B1432132 |
| 13579 | Taro Casnon | 1955.12.12 | M | B1432132 |
| 88231 | Jiro Casnon | 1974.08.24 | M | B2332632 |
| 88231 | Jiro Casnon | 1974.08.24 | M | B2332972 |
| 88231 | Jiro Casnon | 1974.08.24 | M | B2332998 |

ID:  Name:  Search
DOB:  Sex: ● Male ○ Female ○ Other
Start Date: 2008.03.12  Start Time: 10:00:00 to 12:00:00
Modality: DX Cancel  OK

FIG.11

| Trauma | PID | Name | DOB | Acc# |
|---|---|---|---|---|
| Yes | 99999_080314 | 080314 John Doe | | |
| | 88231 | Jiro Canon | 1974.08.24 | B2332632 |
| | 88231 | Jiro Canon | 1974.08.24 | B2332972 |
| | 88231 | Jiro Canon | 1974.08.24 | B2332998 |

| Unknown | Chest PA | Chest AP | Chest LAT |
|---|---|---|---|

PHOTOGRAPHIC INFORMATION PROCESSING APPARATUS AND PHOTOGRAPHIC INFORMATION PROCESSING METHOD

BACKGROUND OF THE INVENTION

1. Field of the Invention

The present invention relates to a photographic information processing apparatus that can process photographic information to be used to capture a medical X-ray image. The present invention further relates to a photographic information processing method and a computer-readable storage medium storing a program.

2. Description of the Related Art

In the medical field, for example, an advanced medical information management system, such as Hospital Information System (HIS) or Radiological Information System (RIS), can be effectively used to process digitized data of medical information. Advanced image acquisition apparatuses functioning as a modality (i.e., a medical device) have remarkable capability for processing digital data of medical images. Typically, a photographing operation for a medical purpose (e.g., X-ray imaging) is generally performed based on examination order information received from the medical information management system (e.g., HIS or RIS).

In general, the modality performs a photographing operation in response to examination order information received from the RIS and outputs the image data acquired in the photographing operation to an image storage server that may be referred to as Picture Archiving and Communication Systems (PACS). The examination order information, for example, includes patient information (e.g., patient ID, patient name, and other personal data) and photographic information (e.g., technical procedure usable in photographing operations).

In case of a medical emergency, it is generally difficult to know a name of a patient or to obtain a properly processed examination order beforehand. For example, in a case where the patient to be photographed is a seriously ill patient, such a patient may not be able to provide personal information. Accordingly, the RIS temporarily generates examination order information based on dummy photographic information to cause the modality to perform a photographing operation based on temporary examination order information. In this case, it may be required that the RIS performs processing for correcting the photographic information after completing the photographing operation.

In addition, there may also exist medical facilities that allow a modality to start a photographing operation before receiving examination order information. In this case, the medical facility receives examination order information after the modality has completed the photographing operation; and the modality corrects the photographic information based on the received examination order information. In many cases, the above-described processing is based on manual work performed by an operator, which is not included in an ordinary workflow and is not performed efficiently. As the photographing operation performed by the modality is done by manual work, it is not discriminated from an ordinary photographing operation. Therefore, image data may be erroneously output together with the dummy photographic information even in a case where the photographic information of the image data needs to be corrected upon completing the photographing operation.

SUMMARY OF THE INVENTION

According to an aspect of the present invention, a photographic information processing apparatus corrects photographic information after completing a photographing operation based on temporarily determined photographic information relating to the photographing operation. The photographic information processing apparatus includes a photographic information correction determination unit configured to determine whether correction of the photographic information is required based on an operation by an operator, an image data acquisition unit configured to detect an X-ray having penetrated a body of a patient and acquire image data based on the detected X-ray, a photographic information correction unit configured to correct the temporarily determined photographic information based on patient information of the patient in a case where the correction of the photographic information is determined to be required by the photographic information correction determination unit, and an image data output unit configured to output prevent the image data acquired by the image data acquisition unit after correction of the temporarily determined photographic information is completed by the photographic information correction unit, wherein the acquired image data is prevented from being output unless the temporarily determined photographic information is corrected.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 6 illustrates an example of the GUI that can be displayed as a photographic information correction screen, which enables users to correct photographic information.

FIG. 11 illustrates an example of a past photographic examination display screen according to the third exemplary embodiment.

DESCRIPTION OF THE EMBODIMENTS

Various exemplary embodiments, features, and aspects of the invention will be described in detail below with reference to the drawings.

Figure 1:
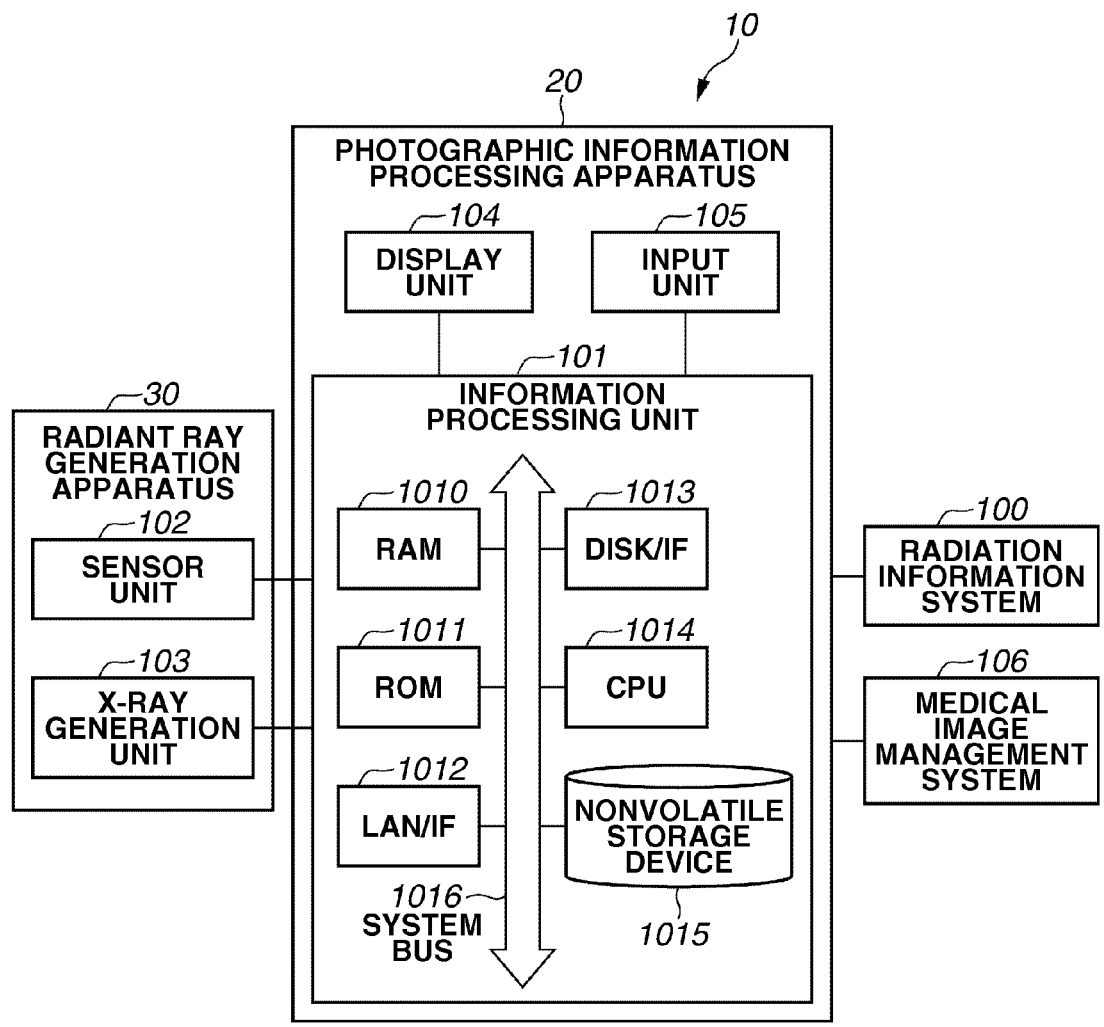
FIG. 1 is a block diagram illustrating an example of a hardware configuration of a photographic information processing system according to an exemplary embodiment of the present invention.

FIG. 1 illustrates an example of a hardware configuration of a photographic information processing system according to an exemplary embodiment of the present invention. As illustrated in FIG. 1, a photographic information processing system 10 includes a photographic information processing apparatus 20, a radiant ray generation apparatus 30, a radiation information system 100, and a medical image management system 106.

The photographic information processing apparatus 20 includes an information processing unit 101, a display unit 104, and an input unit 105. The information processing unit 101 includes a random access memory (RAM) 1010, a read only memory (ROM) 1011, a local area network/interface (LAN/IF) 1012, a DISK/IF 1013, a central processing unit (CPU) 1014, and a nonvolatile storage device 1015 (e.g., a hard disk), which are mutually connected via a system bus 1016.

As described above, the information processing unit 101 is configured as a computer that can be configured to perform particular functions pursuant to instructions from program software, in accordance with the various embodiments of the preset invention. The information processing unit 101 can manage image data and attribute information of images, using a database. The display unit 104 can be constituted by a monitor, such as a cathode ray tube (CRT), a liquid crystal display (LCD) device or the like.

The display unit 104 can display image data and a graphical user interface (GUI) on its screen. The input unit 105 can be constituted by a mouse, a keyboard, and a barcode reader, or other input device configured to receive commands and data from a user. In other words, the input unit 105 enables users to input various commands and data to the information processing unit 101.

The radiant ray generation apparatus 30 includes, for example, an X-ray generation unit 103 and a sensor unit 102. The X-ray generation unit 103 can irradiate a patient with an X-ray. The sensor unit 102 is, for example, a flat panel detector capable of generating an image based on the X-ray having passed through the patient. The radiant ray generation apparatus 30 can transfer acquired image data to the information processing unit 101. If it is desirable, the radiant ray generation apparatus 30 can be integrated with the photographic information processing apparatus 20 as a single radiation photographic apparatus.

The radiation information system 100 is an example of the Radiological Information System (RIS) that can input examination order information to the photographic information processing apparatus 20. The radiation information system 100 is connected to the photographic information processing apparatus 20 via known connecting arrangements, such as, for example, wired or wireless networking. The medical image management system 106 is a medical image server, i.e., an example of the Picture Archiving and Communication Systems (PACS), which can manage image data in accordance with principles of the present invention. The medical image management system 106 can store and manage medical image data that can be transferred from the photographic information processing apparatus 20.

In the photographic information processing system 10, any type of (e.g., wired or wireless) communication means can be employed to mutually connect the photographic information processing apparatus 20, the radiant ray generation apparatus 30, the radiation information system 100, and the medical image management system 106. Further, any type of communication protocol can be used. Any data transmission/reception method can be employed.

Figure 2:
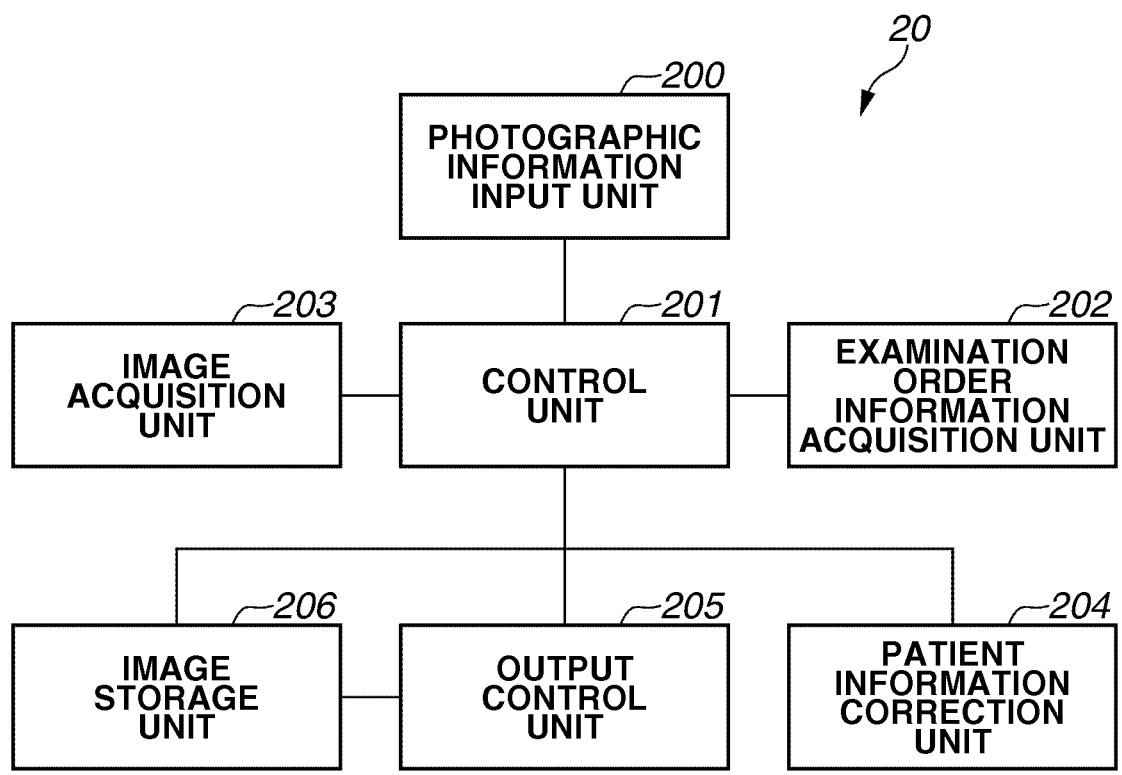
FIG. 2 is a block diagram illustrating an example of a functional configuration of a photographic information processing apparatus according to an exemplary embodiment of the present invention.

Next, a functional configuration of the photographic information processing apparatus according to the present exemplary embodiment is described below. FIG. 2 illustrates an example of the functional configuration of the photographic information processing apparatus 20.

The functional configuration of the photographic information processing apparatus 20 includes a photographic information input unit 200, a control unit 201, an examination order information acquisition unit 202, an image acquisition unit 203, a patient information correction unit 204, an output control unit 205, and an image storage unit 206. To realize the above-described functional configuration, the CPU 1014 of the photographic information processing apparatus 20 executes a program stored in the ROM 1011 or the nonvolatile storage device 1015.

The photographic information input unit 200 can determine the content of each instruction input by an operator via the input unit 105. In particular, the photographic information input unit 200 determines whether to update dummy photographic information that has been temporarily used for a photographing operation based on an operator's instruction input via the input unit 105, to obtain correct photographic information after completing the photographing operation.

The control unit 201 can control various operations to be performed by the photographic information processing apparatus 20 based on operator's instructions input via the input unit 105. Further, the control unit 201 can perform other photographic operations. For example, the control unit 201 generates a drive command to be transmitted to the sensor unit 102 of the radiant ray generation apparatus 30. Further, the control unit 201 searches examination order information while accessing the medical image management system 106.

The examination order information acquisition unit 202 can acquire examination order information from the medical image management system 106 based on an instruction from the control unit 201. In general, acquisition of the examination order information can be performed by acquiring a modality work list, which is defined according to "Digital Imaging and Communication in Medicine" (DICOM), which is a standard specification applied to medical images and communications.

The image acquisition unit 203 can acquire image data based on an instruction supplied from the control unit 201. More specifically, when the image acquisition unit 203 receives an irradiation start instruction from an operator, the image acquisition unit 203 causes the X-ray generation unit 103 of the radiant ray generation apparatus 30 to irradiate a patient with an X-ray. Then, the image acquisition unit 203 acquires image data from the sensor unit 102 of the radiant ray generation apparatus 30 that receives the X-ray having penetrated a body of the patient.

The image storage unit 206 can manage the image data acquired by the image acquisition unit 203 using a database and store the acquired image data in a hard disk or the nonvolatile storage device 1015. After a photographing operation is performed, and photographic information thereof is temporarily stored, based on dummy photographic information, the patient information correction unit 204 can correct the photographic information based on the examination order information acquired by the examination order information acquisition unit 202.

The output control unit 205 can control the output of image data having been captured. More specifically, if it is determined that the correction of the photographic information by the photographic information input unit 200 is necessary, the output control unit 205 prevents the image data from being output unless the correction of the photographic information is completed by the patient information correction unit 204.

Figure 3:
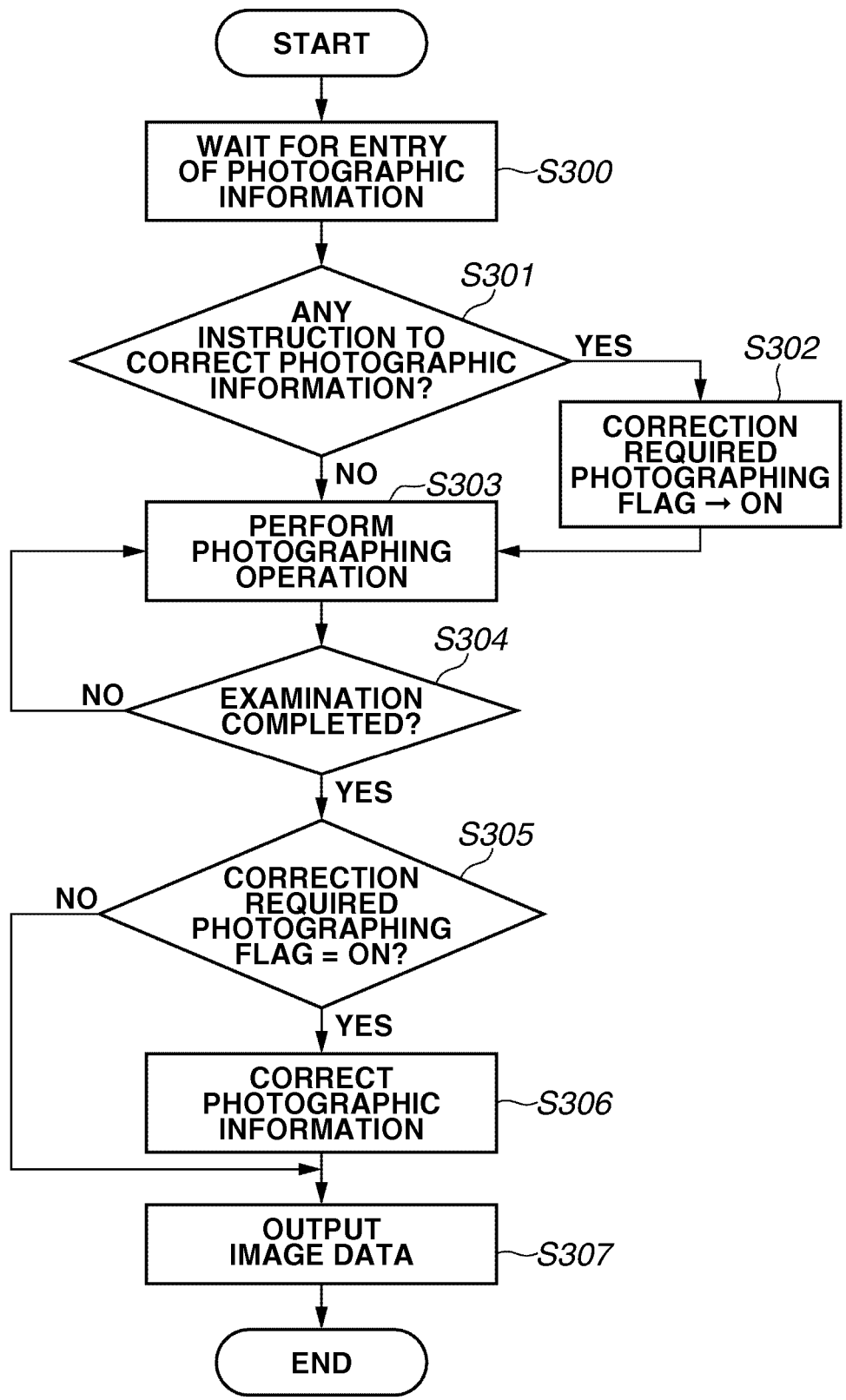
FIG. 3 is a flowchart illustrating an example of operational processing that can be performed by the photographic information processing apparatus according to an exemplary embodiment of the present invention.

Next, operational processing to be performed by the photographic information processing apparatus according to the present exemplary embodiment is described below. FIG. 3 is a flowchart illustrating an example of the operational processing that can be performed by the photographic information processing apparatus 20.

Example processing of the flowchart illustrated in FIG. 3 includes starting a photographing operation and outputting image data. Detailed contents of respective operational processing are described below with reference to flowcharts illustrated in FIG. 7 and FIG. 8. To realize the processing of the flowchart illustrated in FIG. 3, the CPU 1014 of the photographic information processing apparatus 20 executes a program stored in the ROM 1011 or the nonvolatile storage device 1015.

First, in step S300, the photographic information input unit 200 waits for photographic information entered from an operator via the input unit 105. More specifically, the operator inputs photographic information prior to an examination to be performed. The photographic information required beforehand, for example, includes patient information (e.g., patient name, patient identification (ID), date of birth, and sex distinction) and technical information (e.g., technical procedure usable in photographing operations).

In general, the operator does not start a photographing operation unless the entry of the photographic information is thoroughly completed. However, in a case where a seriously ill patient is transported by emergency transport, patient information (i.e., a part of the photographic information) may not be readily available. In such a case, the operator can input dummy photographic information via the input unit 105 and also can input a correction instruction to correct the photographic information after completing the photographing operation.

As an example method for inputting photographic information, the examination order information acquisition unit 202 can request the radiation information system 100 to transmit examination order information and can select examination order information from a list of the received examination order information. Alternatively, the operator can manually input a patient name and a patient ID.

Next, in step S301, the photographic information input unit 200 determines whether there is a correction instruction to correct photographic information after completing the photographing operation. The processing to be executed in step S301 is an example of processing that can be realized by a photographic information correction determination unit according to an exemplary embodiment. If the photographic information input unit 200 determines that the correction instruction is present (YES in step S301), the processing proceeds to step S302. On the other hand, if the photographic information input unit 200 determines that there is not any correction instruction (NO in step S301), the processing proceeds to step S303.

In step S302, the control unit 201 stores information indicating the necessity of correcting the photographic information after completing a photographing operation to be performed. More specifically, the control unit 201 performs processing for setting a correction required photographing flag to ON. Subsequently, the processing proceeds to step S303.

In step S303, the image acquisition unit 203 acquires image data based on an instruction from the control unit 201. The processing to be executed in step S303 is an example of processing that can be realized by an image data acquisition unit according to an exemplary embodiment. The radiant ray generation apparatus 30 performs processing for irradiating a patient with an X-ray and capturing an X-ray image based on a detection signal representing the X-ray having penetrated a body of the patient according to an ordinary method.

More specifically, when an operator activates the radiant ray generation apparatus 30 (e.g., by pressing an X-ray irradiation button or an X-ray irradiation pedal), the image acquisition unit 203 instructs the radiant ray generation apparatus 30 to start emitting an X-ray. The X-ray generation unit 103 of the radiant ray generation apparatus 30 irradiates a patient with the X-ray.

Then, the sensor unit 102 of the radiant ray generation apparatus 30 receives the X-ray having penetrated the patient and generates image data. Image data for static or dynamic images can be generated. The image acquisition unit 203 acquires the generated image data.

Next, in step S304, the photographic information input unit 200 determines whether a photographing end instruction is input by the operator via the input unit 105. If the photographic information input unit 200 determines that the photographing end instruction is detected (YES in step S304), the processing proceeds to step S305. On the other hand, if the photographic information input unit 200 determines that the photographing end instruction is not detected (NO in step S304), the processing returns to step S303 and the image acquisition unit 203 continuously acquires image data. An example of a case where the processing returns to step S303 and the image acquisition unit 203 continuously acquires image data is the photographing procedure known as fluoroscopy. Fluoroscopy is a type of medical imaging that shows a continuous (dynamic) X-ray image on a display, similar to an X-ray movie, in which the movement of a body part, an instrument or a contrast agent through the body of a patient is shown.

In step S305, the control unit 201 determines whether it is necessary to correct the photographic information after completing the photographing operation. More specifically, the control unit 201 determines whether the correction required photographing flag has been set to ON in step S302. If the control unit 201 determines that the correction required photographing flag has been set to ON (YES in step S305), the processing proceeds to step S306. On the other hand, if the control unit 201 determines that the correction required photographing flag has not been set to ON (NO in step S305), the processing proceeds to step 307.

In step S306, the patient information correction unit 204 corrects the temporarily used dummy photographic information. For example, the patient information correction unit 204 corrects the patient information (e.g., patient name) included in the photographic information. The processing to be executed in step S306 is an example of processing that can be realized by a photographic information correction unit according to an exemplary embodiment. A detailed content of the processing to be executed in step S306 is described below with reference to the flowchart illustrated in FIG. 7.

In step S307, the output control unit 205 transfers (i.e., outputs) the captured image data, for example, to the medical image management system 106. More specifically, if the captured image data is based on temporarily determined photographic information, the output control unit 205 outputs the image data on condition that the correction has been completed. More specifically, the output control unit 205 prevents the captured image data from being output unless the correction of the temporarily determined photographic information is completed. The processing to be executed in step S307 is an example of processing that can be realized by an image data output unit according to an exemplary embodiment.

Next, examples of the GUI that can be displayed on the display unit 104 when the photographic information processing apparatus 20 performs operational processing according to the flowchart illustrated in FIG. 3 are described below with reference to FIG. 4, FIG. 5, and FIG. 6. The examples of the GUI illustrated in FIG. 4, FIG. 5, and FIG. 6 are displayed on the display unit 104 when the control unit 201 executes a program stored in the ROM 1011 or the nonvolatile storage device 1015.

Figure 4:
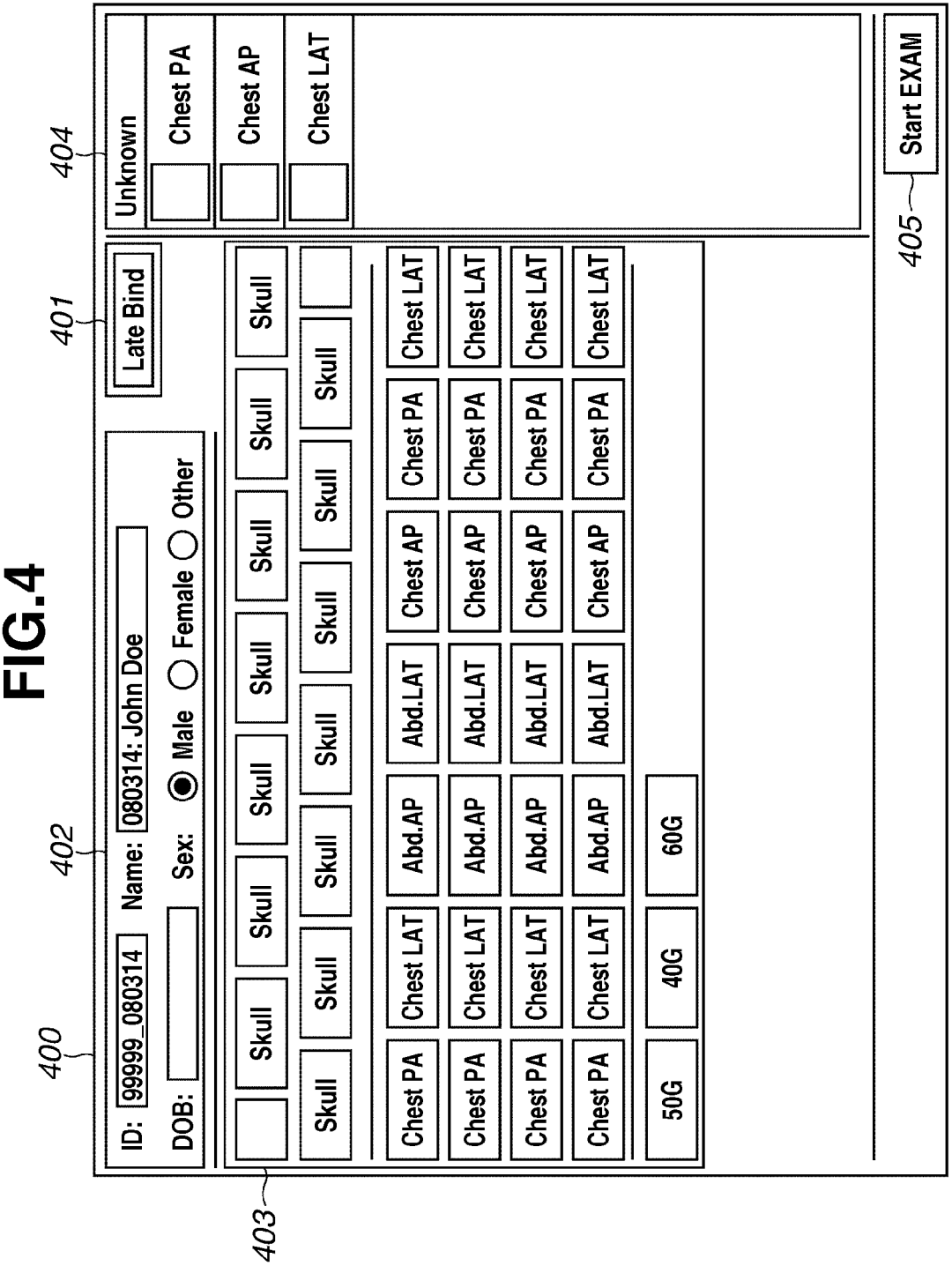
FIG. 4 illustrates an example of a graphical user interface (GUI) that enables users to input photographic information.
Figure 5:
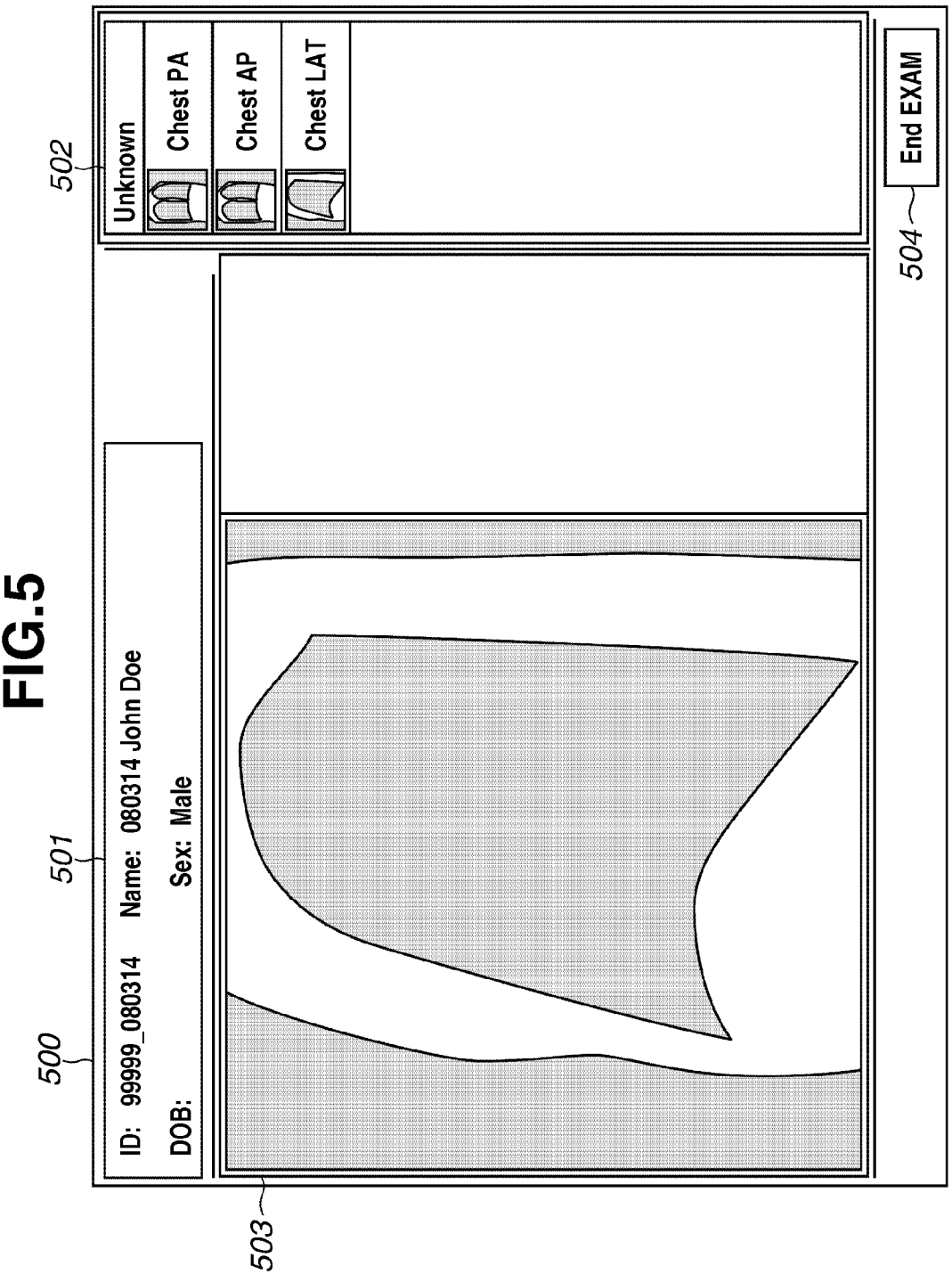
FIG. 5 illustrates an example of the GUI that can be displayed as a photographed image screen.

FIG. 4 illustrates an example of the GUI that enables users to input photographic information in step S300 of the flowchart illustrated in FIG. 3.

Before starting a photographing operation, the operator can input various information on a photographing preparation screen 400 illustrated in FIG. 4. The operator can manipulate a mouse to click on a correction instruction button 401, for example, in a case where a photographing operation to be performed for a patient is based on temporarily determined dummy photographic information. By pressing the correction instruction button 401, the operator can input an instruction to correct the photographic information after completing the photographing operation. The photographic information input unit 200 determines that the correction instruction has been input to correct the photographic information after completing the photographing operation.

Further, the photographing preparation screen 400 includes a patient information input area 402 as a field that enables users to input personal information of a patient to be photographed (e.g., name, ID, date of birth, and sex distinction). When the photographic information input unit 200 detects an operator's click operation on the correction instruction button 401, the photographic information input unit 200 inputs dummy patient information (e.g., a dummy patient name and a dummy ID).

Further, the photographing preparation screen 400 includes a photographic condition input area 403 that enables users to input photographic conditions for a photographing operation to be performed. The photographic condition input area 403 includes various input buttons that can be operated to select a portion to be photographed, a sensor to be used, and an orientation of each sensor.

Further, the photographing preparation screen 400 includes a display area 404 that can display detailed information of a photographing operation to be performed. The photographic information input unit 200 adds detailed photographic information in the display area 404 when photographic conditions are selected in the photographic condition input area 403.

A completion button 405 can be operated to notify completion of the above-described photographing start preparation. When the operator clicks on the completion button 405, the control unit 201 controls the radiant ray generation apparatus 30 to perform a photographing operation based on the input photographic information, and causes the display unit 104 to display a photographed image screen illustrated in FIG. 5.

FIG. 5 illustrates an example of the photographed image screen, which is the GUI that can be displayed on the display unit 104.

A photographed image screen 500 illustrated in FIG. 5 is displayed when the photographing operation is performed. The photographed image screen 500 includes a patient information display area 501 in which the control unit 201 can display patient information based on image data currently used for the photographing operation. According to the example illustrated in FIG. 5, dummy patient information is displayed in the patient information display area 501.

The photographed image screen 500 includes a list display area 502 that can display a list of photographed image data. The control unit 201 displays image data, when acquired by the image acquisition unit 203, in the list display area 502. The photographed image screen 500 further includes an image display area 503. The control unit 201 displays an enlarged image in the image display area 503 based on the image data acquired by the image acquisition unit 203. When the photographing operation is thoroughly completed, the operator can click on an examination termination button 504 to terminate the photographic examination.

FIG. 6 illustrates an example of the GUI that can be displayed as a photographic information correction screen, when the operator corrects the photographic information in step S306 of the flowchart illustrated in FIG. 3. The photographic information correction screen illustrated in FIG. 6 is displayed immediately after the examination termination button 504 illustrated in FIG. 5 is clicked in a state where the correction instruction button 401 illustrated in FIG. 4 is selected.

A photographic information correction screen 600 illustrated in FIG. 6 enables users to correct photographic information.

The photographic information correction screen 600 includes a search condition input area 601 that enables users to input search conditions for the examination order information stored in the radiation information system 100. The search conditions, for example, include the patient information (e.g., patient name, patient ID, date of birth, and sex distinction) and additional information relevant to the photographic information, such as examination date (photographing date), examination time (photographing time), and modality information.

The photographic information correction screen 600 includes a search start button 602 that can be operated to instruct the control unit 201 to start processing for acquiring examination order information. The operator can click on the search start button 602 after completing the entry of search conditions in the search condition input area 601. The photographic information input unit 200 acquires the search conditions having been input by the operator. The above-described processing performed by the photographic information input unit 200 corresponds to an example of the processing to be executed by a search condition acquisition unit according to an exemplary embodiment. The examination order information acquisition unit 202 acquires examination order information that satisfies the search conditions.

The photographic information correction screen 600 includes an examination order information display area 603 that can display a list of acquired examination order information. In the present exemplary embodiment, the examination order information includes patient information (e.g., patient name, patient ID, date of birth, and sex distinction) as illustrated in FIG. 6. The operator selects target examination order information to be used for the correction of the photographic information from the examination order information displayed in the examination order information display area 603, and then the operator clicks on an OK button 605. The patient information correction unit 204 corrects the photographic information including the patient information based on the selected examination order information.

The photographic information correction screen 600 includes a "Cancel" button 604. The operator can click on the "Cancel" button 604 to close the photographic information correction screen 600 without acquiring any examination order information. In this case, the patient information correction unit 204 stores the temporarily determined dummy photographic information without correcting the patient information included therein.

The acquisition of examination order information is not limited to the above-described case in which the search start button 602 is pressed by the operator. It is desired to acquire examination order information in the process of automatically performing a search operation based on the search conditions having been set beforehand when the examination termination button 504 illustrated in FIG. 5 is pressed. More specifically, it is desired that the examination order information display area 603 displays at least one piece of examination order information in an initial display state of the photographic information correction screen 600 illustrated in FIG. 6. Example processing for automatically performing a search operation is described below with reference to a below-described flowchart.

Figure 7:
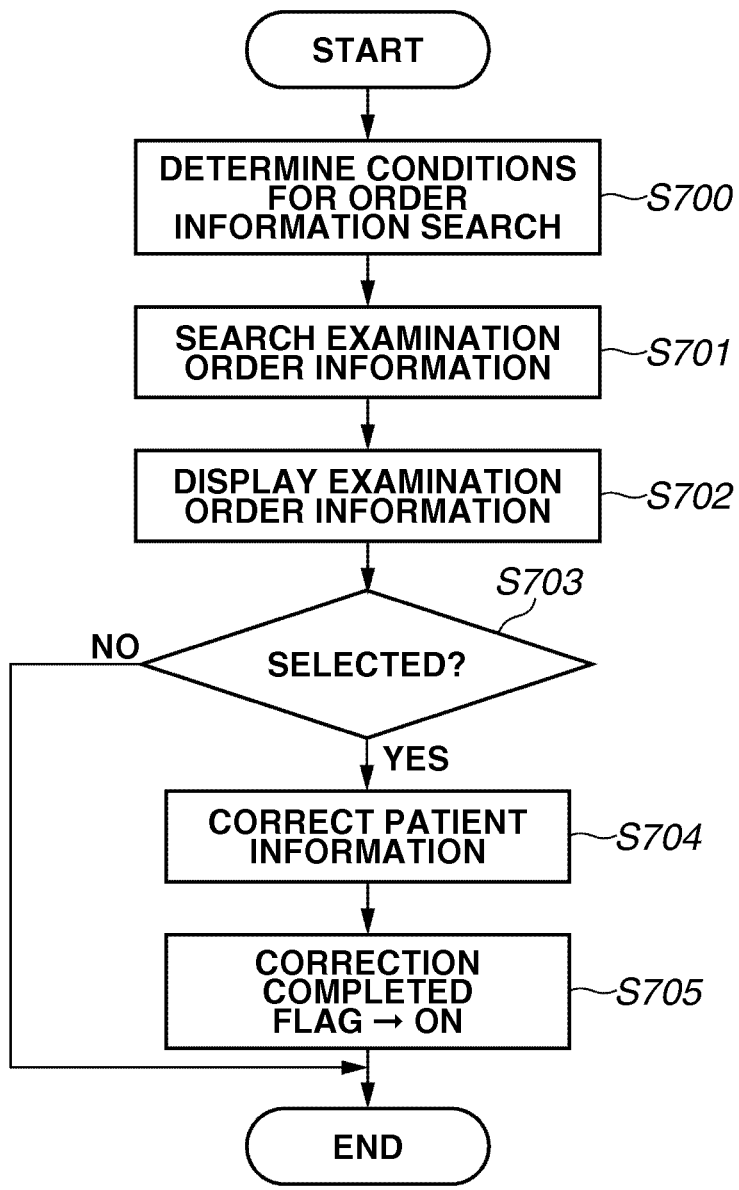
FIG. 7 is a flowchart illustrating an example of information correction processing according to an exemplary embodiment of the present invention.

Next, information correction processing according to the present exemplary embodiment is described below. FIG. 7 is a flowchart illustrating an example of the information correction processing that can be performed by the photographic information processing apparatus 20. The flowchart illustrated in FIG. 7 is detailed processing to be performed in step S306 of the flowchart illustrated in FIG. 3. To realize the processing of the flowchart illustrated in FIG. 7, the CPU 1014 of the photographic information processing apparatus 20 executes a program stored in the ROM 1011 or the nonvolatile storage device 1015.

First, in step S700, the examination order information acquisition unit 202 generates search conditions for searching examination order information based on photographic information relating to a photographing operation having been performed as well as based on additional information relevant to the photographic information. The processing to be executed in step S700 is an example of processing that can be realized by a search condition generation unit according to an exemplary embodiment.

The additional information includes, for example, examination date (photographing date), examination time (photographing time), and modality information. Further, the additional information can include instruction related information that indicates the presence of a correction instruction to correct photographic information after completing the photographing operation. In this case, the radiation information system 100 sets a correction instruction flag as part of processing for generating the examination order information. The examination order information acquisition unit 202 can search corresponding examination order information referring to the correction instruction flag.

It is useful to determine search conditions based on the search conditions in the search condition input area 601, which are manually input by the operator, as illustrated in FIG. 6.

In step S701, the examination order information acquisition unit 202 searches the examination order information generated by the radiation information system 100 based on the determined search conditions. The processing to be executed in step S701 is an example of processing that can be realized by an examination order information search unit according to an exemplary embodiment.

In step S702, the examination order information acquisition unit 202 acquires examination order information that satisfies the search conditions. The processing to be executed in step S702 is an example of processing that can be realized by an examination order information acquisition unit according to an exemplary embodiment. The control unit 201 displays a list of examination order information acquired by the examination order information acquisition unit 202 in the examination order information display area 603, as illustrated in FIG. 6. The processing to be executed in step S702 is an example of processing that can be realized by an examination order information display processing unit according to an exemplary embodiment.

In step S703, the photographic information input unit 200 determines whether there is any examination order information selected by the operator via the input unit 105. The operator confirms the displayed examination order information, and selects examination order information that corresponds to the examination order information obtained in the photographing operation performed based on the temporarily determined dummy photographic information.

If the photographic information input unit 200 determines that the examination order information selected by the operator is present (YES in step S703), the processing proceeds to step S704. If it is determined that there is not any examination order information selected by the operator (NO in step S703), the photographic information input unit 200 terminates the photographic information correction processing. The processing to be executed in step S703 is an example of processing that can be realized by an examination order information selection detection unit according to an exemplary embodiment.

In step S704, the patient information correction unit 204 acquires patient information based on the selected examination order information. Then, the patient information correction unit 204 performs processing for updating the temporarily determined dummy photographic information based on the acquired patient information, to obtain correct photographic information.

In step S705, the patient information correction unit 204 sets a correction completion flag to ON to notify the control unit 201 of completion of the photographic information correction processing and terminates the processing steps illustrated in FIG. 7 (i.e., the information correction processing of step S306 illustrated in FIG. 3).

Figure 8:
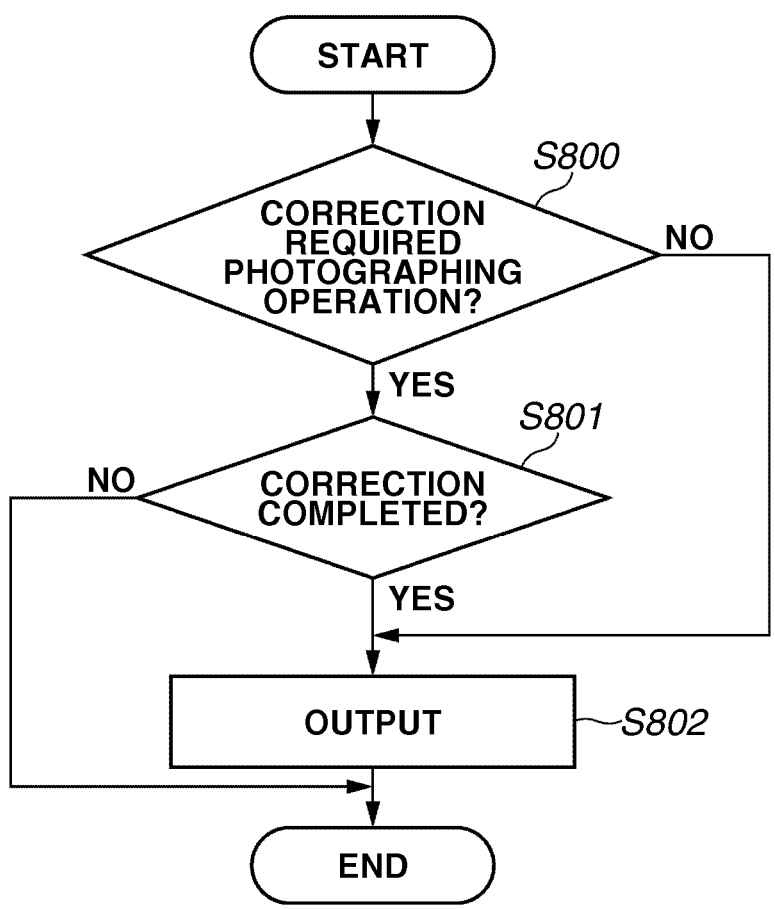
FIG. 8 is a flowchart illustrating an example of output processing according to an exemplary embodiment of the present invention.

Next, output processing according to the present exemplary embodiment is described below. FIG. 8 is a flowchart illustrating an example of the output processing that can be performed by the photographic information processing apparatus 20. The flowchart illustrated in FIG. 8 is detailed processing to be performed in step S307 illustrated in FIG. 3.

First, in step S800, the output control unit 205 determines whether the photographing operation of output target image data is a photographing operation that requires correction of the photographic information after completing the photographing operation. To perform the determination in step S800, the output control unit 205 can check whether the correction required photographing flag has been set to ON in step S302 of the flowchart illustrated in FIG. 3.

If the output control unit 205 determines that the photographing operation requires correction of the photographic information (YES in step S800), the processing proceeds to step S801. If the output control unit 205 determines that the photographing operation does not require any correction of the photographic information (NO in step S800), the processing proceeds to step S802.

In step S801, the output control unit 205 determines whether the correction of the photographic information has been completed. To perform the determination in step S801, the output control unit 205 can check whether the correction completion flag has been set to ON in step S705 of the flowchart illustrated in FIG. 7.

If the output control unit 205 determines that the correction of the photographic information has been completed (YES in step S801), the processing proceeds to step S802. On the other hand, if it is determined that the correction of the photographic information has not been completed (NO in step S801), the output control unit 205 does not output any image data and terminates the processing steps illustrated in FIG. 8 (i.e., the output processing of step S307 illustrated in FIG. 3).

In step S802, the output control unit 205 outputs the image data to the medical image management system 106 or to a printer. In a case where the output control unit 205 outputs the image data to the medical image management system 106, the output control unit 205 associates the image data with the corrected photographic information or the corrected examination order information.

As described above, according to the present exemplary embodiment, an operator can instruct beforehand to perform correction of photographic information after completing a photographing operation. The photographic information processing apparatus controls the radiant ray generation apparatus to perform the photographing operation based on dummy information. Then, the photographic information processing apparatus corrects the photographic information after the radiant ray generation apparatus completes the photographing operation. Further, the photographic information processing apparatus prevents the captured image data from being output unless the correction of the photographic information is completed. Therefore, the present exemplary embodiment can prevent the operator from erroneously outputting the captured image data before the correction of corresponding temporarily determined photographic information is completed.

Further, in a case where the correction of the photographic information is performed, the photographic information processing apparatus automatically acquires examination order information based on appropriate search conditions after completing the photographing operation. Therefore, it is unnecessary for the operator to instruct acquiring the examination order information. Therefore, the present exemplary embodiment can improve the operability.

The examination order information to be used to correct temporarily determined dummy photographic information includes various types of information. For example, the examination order information includes ID information that identifies "Study" of DICOM and a reception number. In the present exemplary embodiment, the "Study" represents an examination unit included in a medical examination order. One medical examination order includes a plurality of examination units ("Studies").

In a case where the examination order information acquired in step S701 of the flowchart illustrated in FIG. 7 includes a plurality of "Studies", the photographic information processing apparatus 20 cannot automatically determine a correspondence between an already performed photographing operation and a "Study" included in the examination order information.

Accordingly, the operator is required to specify one of the plurality of "Studies" as a "Study" corresponding to the photographed image data. In the present exemplary embodiment, the operator can easily perform an operation for associating photographed image data with a corresponding "Study."

Figure 9:
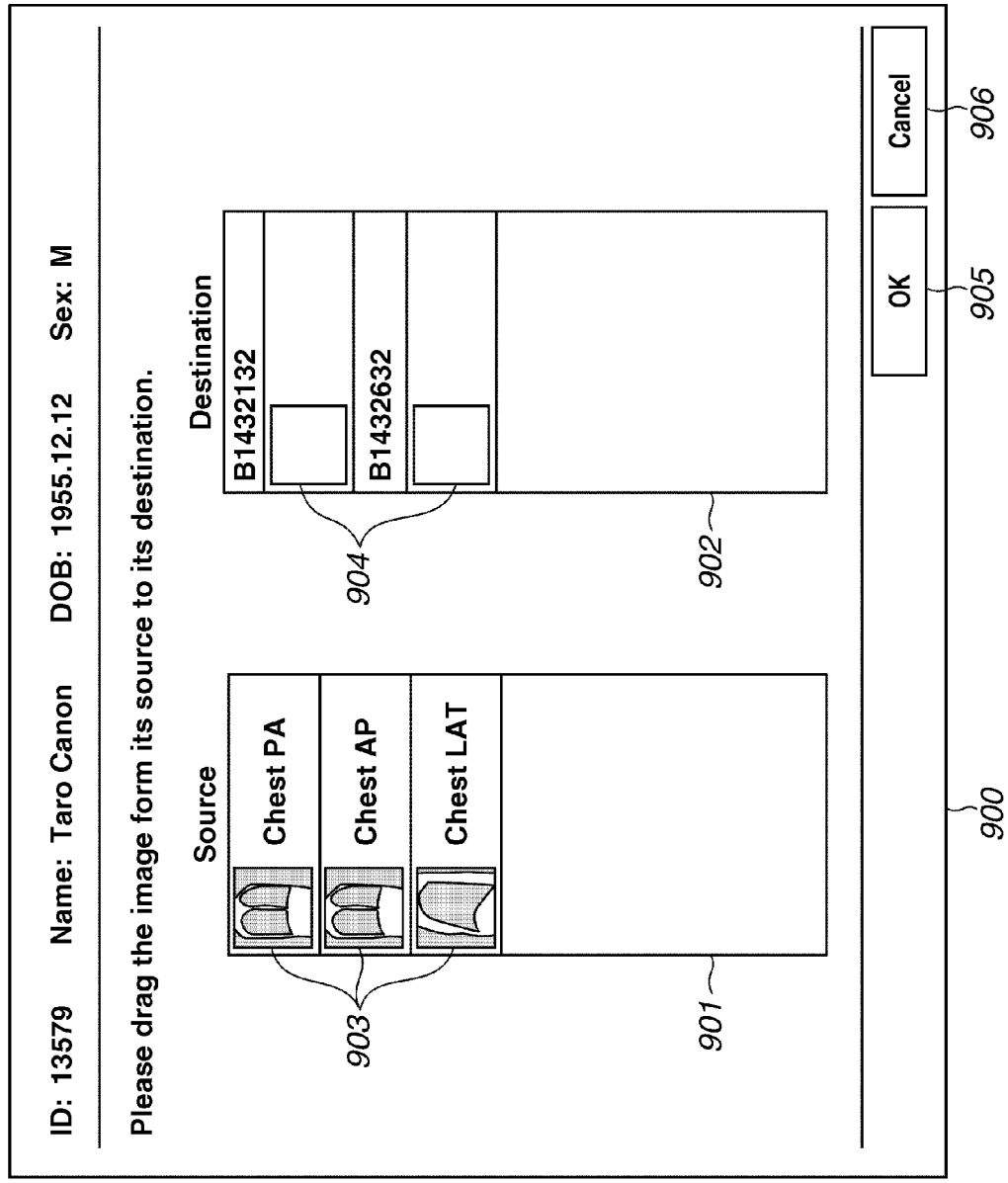
FIG. 9 illustrates an example of the GUI that can be displayed to input an instruction to associate photographed image data with a corresponding "Study" according to a second exemplary embodiment of the present invention.

FIG. 9 illustrates an example of the GUI that enables users to associate the image data obtained through the photographing operation performed in the first exemplary embodiment with the corresponding "Study." The GUI illustrated in FIG. 9 can be displayed when the control unit 201 executes a program stored in the ROM 1011 or the nonvolatile storage device 1015.

The operator can use a replacement screen 900 illustrated in FIG. 9 to manually correct photographic information having been used in the photographing operation. The replacement screen 900 includes an executed photographing display area 901 in which a list of image data of photographing operations having been performed can be displayed. The replacement screen 900 further includes an examination order information display area 902 in which the examination order information selected in step S703 illustrated in FIG. 7 can be displayed.

ID information of each "Study" that serves as examination unit information is displayed in the examination order information display area 902. Each icon 903 represents a reduced image data having been acquired. Each "Study" box 904 is paired with a corresponding ID of the "Study" included in the examination order information.

The operator can manipulate the mouse to drag a target icon 903 and drop it into the "Study" box 904, thereby performing a sorting work for associating photographed image data with its corresponding "Study" included in the examination order information. If the operator clicks on an OK button 905 after thoroughly finishing the above-described sorting operation, the control unit 201 detects the sorting work having been performed to associate the photographic data with its corresponding "Study." The above-described processing is an example of processing that can be realized by an association sorting detection unit according to an exemplary embodiment.

Further, when the control unit 201 detects the above-described sorting operation, the control unit 201 performs replacement processing for associating the photographic data with its corresponding "Study." The above-described processing is an example of processing that can be realized by an association determination unit according to an exemplary embodiment.

The replacement screen 900 includes a "Cancel" button 906. The operator can click on the "Cancel" button 906 if the operator does not perform the above-described association between image data and the "Study." In response to the operation of the "Cancel" button 906, the control unit 201 closes the replacement screen 900.

As described above, according to the present exemplary embodiment, in a case where the acquired examination order information includes a plurality of "Studies", the operator can perform the operation for manually sorting the image data using the GUI after finishing the photographing operation. Accordingly, the operator can easily associate image data with a relevant "Study."

In the present exemplary embodiment, the operator manually sorts the image data to identify a corresponding "Study" of a plurality of "Studies" included in the examination order information. However, the present invention is not limited to the above-described exemplary embodiment. The above-described image data sorting operation can be automatically performed. In this case, for example, the control unit 201 can associate the image data with its corresponding "Study" based on the examination order information. The above-described processing according to the present exemplary embodiment can improve the operability.

According to the first exemplary embodiment, the examination order information display area 603 illustrated in FIG. 6 is displayed in step S306 of the flowchart illustrated in FIG. 3. However, if the medical facility using the photographic information processing apparatus according to the present exemplary embodiment is a small facility, a single operator may perform the above-described operation for inputting photographic information and examination order information. In this case, the operator inputs examination order information after completing a photographing operation. Therefore, no examination order information is present at the moment when the photographing end instruction is input even when the processing for acquiring the examination order information is performed.

Hence, the present exemplary embodiment enables users to use examination order information used in a past photographing operation to correct the temporarily determined dummy photographic information. Further, the present exemplary embodiment enables users to set an instruction whether to correct the photographic information immediately after completing the photographing operation to change the timing for displaying examination order information.

Figure 10:
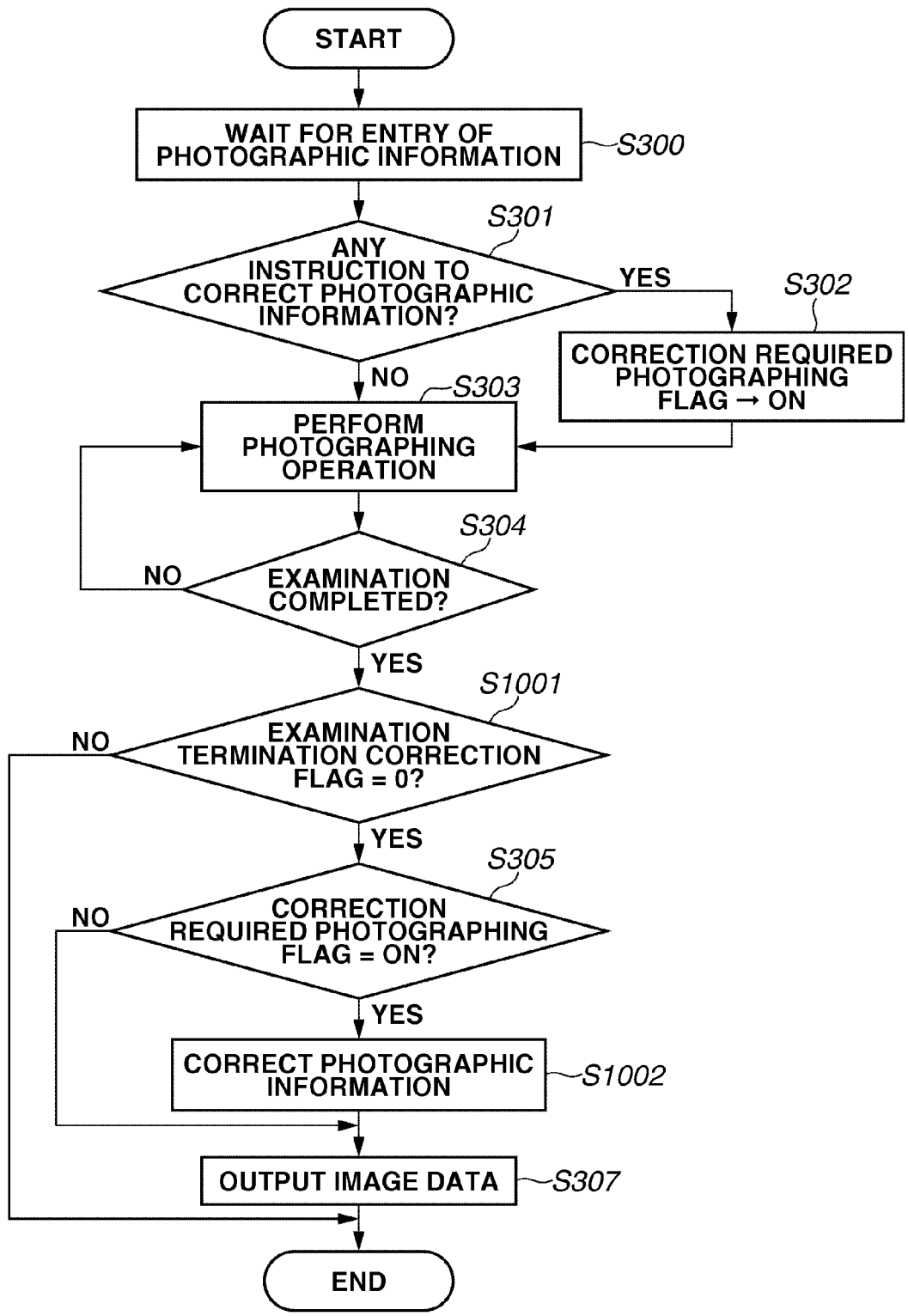
FIG. 10 is a flowchart illustrating an example of operational processing that can be performed by a photographic information processing apparatus according to a third exemplary embodiment of the present invention.

FIG. 10 is a flowchart illustrating an example of operational processing that can be performed by the photographic information processing apparatus 20 according to the present exemplary embodiment. The flowchart illustrated in FIG. 10 is different from the flowchart illustrated in FIG. 3 in that processing of step S1001 is newly added between step S304 and step S305. Further, the flowchart illustrated in FIG. 10 is different from the flowchart illustrated in FIG. 3 in that step S306 is replaced by step S1002. In the following description, only the processing to be performed in step S1001 and step S1002 is described in detail and the descriptions for the processing to be performed in other steps are not repeated.

In the present exemplary embodiment, it is assumed that the operator sets an "immediately after photographing" correction flag to ON beforehand via the input unit 105 if the operator wants to correct photographic information after completing a photographing operation. In this case, the photographic information input unit 200 detects the ON setting of the "immediately after photographing" correction flag. The above-described processing is an example of processing that can be realized by a setting detection unit according to an exemplary embodiment.

As described below, when the "immediately after photographing" correction flag is set to ON, examination order information is displayed. When the "immediately after photographing" correction flag is not set, examination order information is not displayed. Accordingly, the setting of the "immediately after photographing" correction flag can be regarded as a setting for changing the display timing of the examination order information.

In step S1001, the control unit 201 determines whether to correct the photographic information after completing the photographing operation. More specifically, the control unit 201 determines whether an examination termination correction flag is set to ON.

If the control unit 201 determines that the correction of the photographic information is set to be performed immediately after completing the photographing operation (YES in step S1001), the processing proceeds to step S305. On the other hand, if it is determined that the correction of the photographic information is not set to be performed immediately after completing the photographing operation (NO in step S1001), the control unit 201 skips the correction processing and terminates the processing steps illustrated in FIG. 10. More specifically, the control unit 201 does not perform the following processing for displaying the examination order information. In step S1002, the control unit 201 causes the display unit 104 to display a past photographic examination display screen.

FIG. 11 illustrates an example of the past photographic examination display screen. A past photographic examination display screen 1100 illustrated in FIG. 11 includes a past examination list display area 1101 that displays a list of examinations having been performed in the past. The information displayed in the past examination list display area 1101 includes results of photographic examinations having been performed based on temporarily determined dummy photographic information and not yet subjected to the correction of the photographic information, so that the operator can discriminate individual examination results. In the present exemplary embodiment, if the photographic information is not yet subjected to the correction, "Yes" is displayed in a column "Trauma" of the past examination list display area 1101 illustrated in FIG. 11.

The past photographic examination display screen illustrated in FIG. 11 includes a photographic list display area 1102 that can display a list of image data that corresponds to photographic information selected from the photographic information displayed in the past examination list display area 1101. When the operator performs a double click operation on selected temporarily determined dummy photographic information, the examination order information acquisition unit 202 generates search conditions and acquires past examination order information that satisfies the generated search conditions.

The control unit 201 displays a list of the acquired examination order information in the examination order information display area 603, as illustrated in FIG. 6. Then, as described in the first exemplary embodiment, the patient information correction unit 204 updates the temporarily determined dummy photographic information based on the examination order information selected by the operator to obtain correct photographic information.

As described above, the present exemplary embodiment corrects temporarily determined dummy photographic information based on past examination order information, thereby realizing an optimum workflow according to a status of the medical facility.

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-106388 filed Apr. 24, 2009, which is hereby incorporated by reference herein in its entirety.

What is claimed is:

1. A radiographic information processing apparatus for correcting radiographic information, the apparatus comprising:
   a generation unit configured to generate temporary information included in radiographic information;
   a correction determination unit configured to determine whether correction of the radiographic information is required, by determining the radiographic information includes the generated temporary information;
   a radiography control unit configured to control radiography using a digital X-ray detector based on the radiographic information, to acquire image data;
   a radiographic correction unit configured to correct the generated temporary information based on subject information of the subject to obtain corrected information; and
   an output unit configured to output the acquired image data acquired with corresponding radiographic information; and
   a control unit configured to control the output unit so as to prevent the image data with corresponding radiographic information from being output in a case where the corresponding radiographic information includes the generated temporary information to be corrected.

2. The radiographic information processing apparatus according to claim 1, further comprising:
   an order acquisition unit configured to acquire examination order information that corresponds to the subject,
   wherein the radiographic correction unit is configured to correct the generated temporary information based on the subject information included in the examination order information acquired by the order acquisition unit.

3. The radiographic information processing apparatus according to claim 1, further comprising:
   a search unit configured to search examination order information based on search conditions corresponding to the subject;
   an examination order information display processing unit configured to display the examination order information having been searched by the search unit; and
   a selection detection unit configured to detect examination order information selected by an operator from the examination order information displayed by the examination order information display processing unit,
   wherein the radiographic correction unit is configured to correct the generated temporary information based on the subject information included in the examination order information detected by the selection detection unit.

4. The radiographic information processing apparatus according to claim 3, further comprising:
   a search condition generation unit configured to generate search conditions based on at least one of the generated temporary information and additional information relating to the generated temporary information,
   wherein the search unit is configured to search examination order information based on the search conditions generated by the search condition generation unit.

5. The radiographic information processing apparatus according to claim 3, further comprising:
   a search condition acquisition unit configured to acquire search conditions having been input by the operator,
   wherein search unit is configured to search examination order information based on the search conditions acquired by the search condition acquisition unit.

6. The radiographic information processing apparatus according to claim 2, further comprising:
   an association determination unit configured to associate image data acquired by the image acquisition unit with an examination unit included in the examination order information.

7. The radiographic information processing apparatus according to claim 6, further comprising:
   a display processing unit configured to display examination unit information included in the examination order information and the image data acquired by the image acquisition unit; and
   an association sorting detection unit configured to detect a sorting operation by the operator with respect to an association between the examination unit information displayed by the display processing unit and image data,
   wherein the association determination unit is configured to associate the image data acquired by the image acquisition unit with the examination unit included in the examination order information based on the selection of the association detected by the association sorting detection unit.

8. The radiographic information processing apparatus according to claim 3, further comprising:
   a setting detection unit configured to detect a setting indicating whether to display the examination order information,
   wherein the examination order information display processing unit is configured to change display timing of the examination order information based on the setting having been detected by the setting detection unit.

9. The radiographic information processing apparatus according to claim 3, wherein
   the search unit is configured to detect past examination order information in a case where there is no examination order information that corresponds to the subject, and
   the radiographic correction unit is configured to correct the generated temporary information based on past examination order information detected by the selection detection unit.

10. The radiographic information processing apparatus of claim 1, wherein the generation unit is configured to generate information indicating a region of radiographic imaging as the temporary information.

11. The radiographic information processing apparatus of claim 1, further comprising a display control unit configured to cause a display unit to display the generated temporary radiographic information before irradiation of the subject to be imaged is started.

12. The radiographic information processing apparatus of claim 1, further comprising:
   a receiving unit configured to receive at least one item of radiographic information from a radiology information system; and
   a display control unit configured to control a display unit to display the received, at least one item of radiographic information;
   wherein the radiographic correction unit is configured to correct the generated temporary information by associating the acquired image data and radiographic information, selected from the received, at least one item of radiographic information, according to an input operation.

13. The radiographic information processing apparatus of claim 12, wherein the display control unit is configured to control the display unit to display the received, at least one item of radiographic information, in response to an input operation for finishing radiographic imaging corresponding to the generated temporary information.

14. The radiographic information processing apparatus of claim 1, further comprising a display control unit configured to control a display unit to display a button for receiving an input operation for generating the temporary information by the generation unit, before radiographic imaging is started.

15. The radiographic information processing apparatus of claim 1, further comprising a display control unit configured to control a display unit to display a graphical user interface for receiving an input operation for correcting the generated temporary information.

16. The radiographic information processing apparatus of claim 1, further comprising a display control unit to control a display unit to display a graphical user interface for receiving a first input operation for instructing correction of the generated temporary information, and a second input operation for leaving the generated temporary information to be corrected.

17. A radiographic information processing method for correcting radiographic information, the method comprising:
   generating temporary information included in radiographic information;
   determining, using a processor, whether correction of the radiographic information is required, by determining the radiographic information includes the generated temporary information;
   detecting an X-ray having penetrated a body of a subject and acquiring image data based on the detected X-ray;
   correcting the generated temporary information based on subject information of the subject; and
   outputting the acquired image data with corresponding radiographic information; and
   controlling, using the processor, so that the acquired image data is prevented from being output in a case where the corresponding radiographic information includes the generated temporary information to be corrected.

18. A computer-readable storage medium having computer-executable instructions stored thereon for causing a computer to correct radiographic information, the computer-readable storage medium comprising:
   computer-executable instructions for generating temporary information included in radiographic information;
   computer-executable instructions for determining whether correction of the radiographic information is required, by determining the radiographic information includes the generated temporary information;
   computer-executable instructions for detecting an X-ray having penetrated a body of a subject and acquiring image data based on the detected X-ray;
   computer-executable instructions for correcting the generated temporary information based on subject information of the subject;
   computer-executable instructions for outputting the acquired image data with corresponding radiographic information; and
   computer-executable instructions for controlling so that the acquired image data is prevented from being output in a case where the corresponding radiographic information includes the generated temporary information to be corrected.

19. A photography control apparatus comprising:
   an acquisition unit configured to acquire photographic information for radiography by a digital radiography apparatus;
   a photography control unit configured to control the radiography by the digital radiography apparatus based on the photographic information;
   an output unit configured to output the photographic information and radiographic image data acquired by the radiography based on the photographic information in association with each other;
   a determination unit configured to determine, based on the photographic information, whether subject information in the photographic information should be corrected;
   a display control unit configured to display a screen for requiring correction of the subject information according to a result of the determination; and
   a control unit configured to prevent the radiographic image data acquired by the radiography from being output according to the result of the determination.

20. The photography control apparatus according to claim 19, further comprising:
   a generation unit configured to generate dummy subject information,
   wherein the control unit is configured to control whether the subject information should corrected according to whether the generated dummy subject information is included in the photographic information.

21. The photography control apparatus according to claim 19, further comprising:
   a generation unit configured to generate dummy subject information; and
   an instruction unit configured to issue an instruction for generating the dummy subject information,
   wherein the acquisition unit is configured to acquire the dummy subject information as the photographic information in a case where the instruction unit issues the instruction, and
   wherein the determination unit is configured to determine whether the subject information should be corrected according to whether the dummy subject information is included in the photographic information.

22. The photography control apparatus according to claim 19, further comprising:
   a receiving unit configured to receive photographic information from an external photographic information processing system; and
   a generation unit configured to generate dummy subject information,
   wherein the photography control unit is configured to selectively execute one of a first control mode in which the display unit displays a photographic screen for radiography based on the received subject information and a second control unit in which the display unit displays a photographic screen for radiography based on the generated dummy subject information, and
   wherein the display control unit is configured to display a screen for requiring correction of the subject information according to the result of the determination in a case where the second control unit is selected.

23. The radiographic information processing apparatus of claim 19, further comprising:
   a receiving unit configured to receive at least one item of radiographic information from a radiology information system,
   wherein the display control unit is configured to control a display unit to display the received, at least one item of radiographic information, and the apparatus further comprising:
   a radiographic correction unit configured to correct the subject information by associating the acquired image data and radiographic information, selected from the received at least one item of radiographic information, according to an input operation.

24. The radiographic information processing apparatus of claim 23, wherein the display control unit is configured to control the display unit to display the received at least one item of radiographic information, in response to an input operation for finishing radiography corresponding to the acquired radiographic information.

25. The photography control apparatus of claim 20, wherein the generation unit is configured to generate information indicating a region to be imaged as the dummy subject information.

26. The photography control apparatus of claim 20, wherein the display control unit is configured to cause a display unit to display the generated temporary radiographic information before irradiation of the subject to be imaged is started.

* * * * *